United States Patent [19]

Rulkens et al.

[11] Patent Number: 4,457,807

[45] Date of Patent: Jul. 3, 1984

[54] PROCESS FOR THE PURIFICATION OF ε-CAPROLACTAM

[75] Inventors: Peter F. M. Rulkens; Nicolaas F. Haasen, both of Sittard; Otto G. Plantema, Nederweert, all of Netherlands

[73] Assignee: Stamicarbon B.V., Geleen, Netherlands

[21] Appl. No.: 376,001

[22] Filed: May 7, 1982

[30] Foreign Application Priority Data

May 9, 1981 [NL] Netherlands ......................... 8102280

[51] Int. Cl.$^3$ .......................... B01D 3/10; B01D 3/14
[52] U.S. Cl. ........................................ 203/72; 203/74; 203/89; 203/91; 203/100; 260/239.3 A
[58] Field of Search ................. 260/239.3 R, 239.3 A; 203/91, 99, 71, 72, 73, 74, 81, 89, 100

[56] References Cited

U.S. PATENT DOCUMENTS

| | | | |
|---|---|---|---|
| 3,686,077 | 8/1972 | Dekoning | 203/40 |
| 3,939,153 | 2/1976 | Fowler | 260/239.3 A |
| 4,326,925 | 4/1982 | Senni et al. | 203/37 |

FOREIGN PATENT DOCUMENTS 2035859  3/1971  Fed. Rep. of Germany .

*Primary Examiner*—Frank Sever
*Attorney, Agent, or Firm*—Cushman, Darby & Cushman

[57] ABSTRACT

A process is provided for recovering epsilon-caprolactam of a purity in excess of 99.9 wt. %, in a two-stage distillation operation. Each stage comprises an evaporator and a rectification column having a pressure drop across the theoretical trays thereof of less than about 2.5 MBAR.

6 Claims, No Drawings

PROCESS FOR THE PURIFICATION OF ε-CAPROLACTAM

BACKGROUND OF THE INVENTION

The present invention relates to an improved process for purifying ε-caprolactam, (the starting material for nylon-6), obtained through Beckmann rearrangement of cyclohexanone oxime.

Such ε-caprolactam contains several impurities which must be removed in order to obtain a product suitable for polymerization. This impurity removal is effected in a number of processing steps, usually categorized into a pre-purification and final purification steps. The final purification is normally carried out by subjecting the ε-caprolactam containing impurities but already having a high degree of purity, such as about 99%, to distillation under reduced pressure.

According to German Offenlegungsschrift No. 2035859, dehydrated liquid crude ε-caprolactam can be distilled by employing three rectifiers and three evaporators under non-adiabatic conditions to obtain a purified ε-caprolactam product. The said rectifiers are carried out as thin layer rectification columns in order to minimise thermal degradation.

In practice, however, it has been observed that even greater ε-caprolactam purity is desirable in order to obtain better final polymerization products and to reduce capital costs in processing plants and equipment for handling ε-caprolactam. It has been observed that such a need exists for increasing the purity of caprolactam obtained by the rearrangement of cyclohexanone oxime by means of sulfuric acid or oleum.

The present invention satisfies this need by providing a distillation process for final purification of dehydrated but impure caprolactam (water content less than 1% by wt.) yielding very pure caprolactam and which requires less complicated and less expensive equipment.

SUMMARY OF THE INVENTION

In the process according to the present invention for purifying the ε-caprolactam product obtained by the rearrangement of cyclohexanone oxime with the help of sulfuric acid or oleum, the caprolactam being purified is subjected to distillation under reduced pressure, leading to separation of low-boiling and high-boiling impurities in two steps.

DETAILED DESCRIPTION OF THE INVENTION

In the two stage destillation of impure ε-caprolactam under reduced pressure, the caprolactam to be purified is supplied to the rectification column of the first step, the low-boiling impurities are carried off as top product from this column, the bottom product remaining in the first step or stage is supplied to the second step or stage, the high-boiling impurities are carried off as bottom product in the second step. The desired purified caprolactam is recovered as top product in this second step.

In at least the first step or stage an evaporator is present together with a rectification column which contains packing material such that there is a pressure drop of less than 2.5 millibars across each theoretical tray. By preference the second step or stage also consists of an evaporator and a rectification column containing said packing material. The pressure drop of less than about 2.5 mbar across each theoretic tray relates to measurement under standard conditions, such as rectification of a cis-trans decalin mixture (50% cis and 50% trans) with total reflux at a pressure of 50 mbar and a vapor transport rate of 5.2 m/s (see F. J. Zuiderweg Recommended Test Mixtures for Distillation Column 1969, Institution of Chemical Engineers, which reference is incorporated by reference herein).

Any packing material for the rectification yielding a pressure drop of less than about 2.5 mbar across each theoretic tray is suitable. Such packing materials are commercially available, for instance Intalox metal packing (described in Chemical Engineering Progress, March 1979, pp. 86–91, which reference is incorporated by reference herein), Sulzer packing BX type (see Chemie Ingenieur Technik, part 37, p. 322, 1965, which reference is incorporated by reference herein) and Sulzer Mellapack type packing, (see Chemical Engineering Progress, November 1977, pp. 71–77, which reference is incorporated by reference herein). Preferably a packing material, such as, for instance, the Mellapack type of Sulzer, is used which gives a pressure drop of less than about 1.5 mbar across each theoretical tray.

The number of theoretical trays required in the rectification depends on the desired separation capacity. Usually, about 5 to about 15 theoretical trays in the first step and about 1 to about 5 in the second step (if this step consists of an evaporator and rectification column containing said packing material) are sufficient for obtaining a very high purity polymerizable grade ε-caprolactam.

The caprolactam being purified is supplied to the rectification column of the first step either into the top of the column in the first step or into the column itself at an intermediate point. The bottom product of the first step is supplied to the second step, if this step consists of an evaporator and a rectification column containing said packing material, either to the evaporator or to the rectification column, for instance to the first theoretical tray from the bottom of the column.

Impure caprolactam is not suitable for polymerization. The purity of the untreated captrolactam being distilled in accordance with the invention may be different and usually will be about 95% to about 99.9% pure by weight. If desired, caprolactam products having less than about 95% purity may be distilled in accordance with the invention. However, it is desirable to improve the pre-purification to the extent that prior to the final purification in accordance with the invention, a starting product with a starting purity better than 95% is obtained.

The distillation accordance to the present invention is carried out at reduced pressure which can vary in relation with the desired bottom temperatures. Preferably, a bottom pressure of about 5 mbar to about 70 mbar is maintained in the rectification column of the first step, and a bottom pressure of about 5 to 15 mbar in the rectification column as used by preference in the second step. The bottom temperature of the rectification column in the first step is preferably taken between about 115° C. and 175° C., while the bottom temperature is the rectification column as used by preference in the second step is preferably taken between about 115° C. and 145° C.

EXAMPLES

The invention will be further elucidated in the following non-limiting examples which illustrate various embodiments

EXAMPLE I

In a two-step vacuum distillation installation with in each step a rectification column with a condenser and a falling film evaporator for the heating of the bottom liquid, ε-caprolactam (purity 99.4% by wt.), obtained through rearrangement of cyclohexanone oxime with oleum, is purified. The falling film evaporator used is of the Normag 9318 S type. Sulzer BX type packing (pressure drop 0.7 mbar across each theoretical tray) is used in the rectification columns (diameter 7 cm). 8,827 grams per hour of the untreated caprolactam (containing, as usual in the purification of caprolactam by distillation, 0.2 mg of solid NaOH per gram off caprolactam) is supplied to the fifth theoretical tray (counted form the bottom) of the rectification column of the first step (7.5 theoretical trays). The bottom pressure of the rectification column is 12 mbar. The bottom temperature is 141° C. The rectification column top temperature is 134.5° C. In the falling film evaporator of the first step a heating medium with a temperature of 180° C. is used. In the first step, 466 grams distillate per hour is carried off via the condenser, the reflux ratio being 3. A quantity of 1,972 grams per hour of the bottom product from the first step is supplied to the evaporator of the second step.

In the second step the number of theoretical trays of the rectification column is 2.5. The reflux ratio of 0.3. The bottom pressure in the column is 8 mbar. The temperature in the top of the column is 123° C. while the temperature in the bottom of the column is 133° C. In the falling film evaporator of the second step a heating medium with a temperature of 165.5° C. is used. From the second step 1,780 grams ε-caprolactam per hour, with a purity in excess of 99.9% by weight, is carried off via the condenser. The color index of the purified caprolactam is 3° Hazen (50% by weight aqueous solution), the extinction measured with a layer of 4 cm with light of 290 nm, expressed as the logarithm of the portion of the light which is absorbed) is 0.11 and the permanganate number is above 10,000.

Conducting the above-described distillation with rectification columns lacking packing materials (carried out as falling film evaporator) the product is less pure and had an extinction value of 0.18 and a permanganate number of 7,000.

EXAMPLE II

In the distillation installation as described in Example I, 9,144 grams per hour of ε-caprolactam (purity 99.3% by weight), obtained through rearrangement of cyclohexanone oxime with oleum, is supplied to the fifth theoretical tray of the rectification column of the first step. In the first step, at a bottom pressure of 10 mbar in the rectification column and a reflux ratio of 8,331 grams per hour of distillate is carried off via the condenser. The top temperature in the rectification column in the first step is 133° C. and the bottom temperature is 142.5° C. In the falling film evaporator in the first step a heating medium with a temperature of 180° C. is used. Of the bottom product obtained in the first step, a quantity of 2,255 grams per hour is supplied to the evaporator of the second step. At a bottom pressure of 7.33 mbar in the rectification column of the second step and a reflux ratio of 0.05, 2,145 grams caprolactam per hour with a purity in excess of 99.9% by weight is carried off via the condenser. The top temperature in the rectification column of the second step is 122° C.; the bottom temperature is 134.5° C. In the falling film evaporator of the second step a heating medium with a temperature of 166° C. is used. The final product has a color index of 2° Hazen, extinction value of 0.1 and a permanganate number of more than 10,000.

EXAMPLE III

In a distillation installation such as described in Example I, 8,248 grams per hour of ε-caprolactam (purity 99.5% by weight), obtained through rearrangement of cyclohexanone oxime with oleum, is supplied to the fifth theoretical tray of the rectification column (10 theoretical trays) of the first step. In the first step, at a bottom pressure of 58 mbar in the rectification column and a reflux ratio of 3,446 grams per hour of distillate is carried off via the condenser. The top temperature in the rectification column in the first step is 164° C. and the bottom temperature is 170° C. In the falling film evaporator in the first step a heating medium with a temperature of 214° C. is used. Of the bottom product obtained in the first step, a quantity of 1,848 grams per hour is supplied to the evaporator of the second step. At a bottom pressure of 8 mbar in the rectification column (1 theoretical tray) of the second step and a reflux ratio of 0.3, 1,752 grams caprolactam per hour with a purity in excess of 99.9% by weight is carried off via the condenser. The top temperature in the rectification column of the second step is 122° C.; the bottom temperature is 130° C. In the falling film evaporator of the second step a heating medium with a temperature of 170° C. is used. The final product has a color index of 0° Hazen, extinction value of 0.1 and a permanganate number of more than 10,000.

What is claimed is:

1. A process for purifying a dehydrated ε-caprolactam product obtained by rearrangement of cyclohexanone oxime in the presence of sulfuric acid or oleum by distilling said caprolactam under reduced pressure to separate out low-boiling and high-boiling impurities from said caprolactam to yield a very pure polymerizable grade ε-caprolactam product, said process comprising the combination of steps of:

A. conducting said distillation of untreated ε-caprolactam in a first and in a second stage wherein said first stage and said second stage each includes an evaporator and a rectification column containing packing material such that the pressure drop across each theoretic tray in the respective rectification columns is less than about 2.5 mbar;
   B. supplying said impure caprolactam to said rectification column in said first stage;
   C. separating out as a top product the low-boiling impurities from said caprolactam in said rectification column in said first stage while leaving caprolactam containing high-boiling impurities as a bottom product;
   D. feeding said bottom product to said second stage and separating out the high-boiling impurities from the caprolactam in said bottom product; and
   E. recovering polymerizable grade ε-caprolactam having purity greater than 99.9 weight percent as a top product in said second stage.

2. Process according to claim 1 wherein a bottom temperature of about 115° to about 175° C. is applied in the rectification column of the first stage, while a bottom temperature of about 115 to about 145° C. is applied in the rectification column of the second stage.

3. A two stage process for purifying a dehydrated impure ε-caprolactam product obtained by rearrangement of cyclohexanone oxime in the presence of sulfuric acid or oleum by distilling the impure ε-caprolactam under reduced pressure to separate out low-boiling and high-boiling impurities to thereby yield a very pure polymerizable grade ε-caprolactam product, said process comprising the combination of steps of:

A. supplying said impure ε-caprolactam to a first stage and then distilling said impure ε-caprolactam in said first stage, said first stage including an evaporator and a rectification column, said rectification column containing packing material such that the pressure drop cross each theoretical tray therein is less than about 1.5 mbar, said first stage rectification column having a bottom temperature of about 115° C. to about 175° C.;

B. separating out as a top product the low-boiling impurities from said impure ε-caprolactam in said first stage rectification column while leaving a bottom product containing ε-caprolactam and high boiling impurities;

C. feeding said bottom product from said first stage to a second stage and then distilling said bottom product in said second stage, said second stage including an evaporator and a rectification column, said second stage rectification column containing packing material such that the pressure drop across each theoretical tray therein is less than about 1.5 mbar, said rectification column having a bottom temperature of about 115° C. to about 145° C.;

D. separating out a second stage bottom product from said bottom product of step (b) in said second stage rectification column, said second stage bottom product containing the high-boiling impurities; and E. recovering polymerizable grade ε-caprolactam having a purity greater than 99.9 weight percent as a top product from said second stage rectification column.

4. Process according to any one of the claims 1 or 3 wherein said initial impure caprolactam supply to said first stage is about 95% to about 99.9% pure by weight.

5. Process according to any one of the claims 1 or 3 wherein a bottom pressure of about 5 mbar to about 70 mbar is applied in the rectification column of the first stage, and a bottom pressure of about 5 to about 15 mbar is applied in the rectification column of the second stage.

6. Process according to claim 1 or 3 wherein said impure ε-caprolactam supply to said first stage is about 95% to 99.9% pure by weight, said first stage rectification column having a bottom pressure of about 5 mbar to about 70 mbar, and said second stage rectification column having a bottom pressure of about 5 to about 15 mbar.

* * * * *